United States Patent
Sanders et al.

(10) Patent No.: US 10,729,843 B2
(45) Date of Patent: Aug. 4, 2020

(54) DUAL PACKAGING FOR FILL NEEDLE AND SAFETY NEEDLE

(71) Applicant: Becton, Dickinson and Company, Franklin Lakes, NJ (US)

(72) Inventors: Laurie Sanders, Glen Ridge, NJ (US); Edward P. Browka, Oneida, NY (US); Peter Smith, Cary, NC (US); Adam Kristopher Brakoniecki, Hawthorne, NJ (US); Alice Wong, Leonia, NJ (US); Regina Haywood, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 17 days.

(21) Appl. No.: 15/837,012

(22) Filed: Dec. 11, 2017

(65) Prior Publication Data

US 2018/0161490 A1  Jun. 14, 2018

Related U.S. Application Data

(60) Provisional application No. 62/433,044, filed on Dec. 12, 2016.

(51) Int. Cl.
| | | |
|---|---|---|
| *A61M 5/00* | (2006.01) | |
| *B65D 77/20* | (2006.01) | |
| *B65D 75/32* | (2006.01) | |
| *A61M 5/32* | (2006.01) | |

(52) U.S. Cl.
CPC .......... *A61M 5/002* (2013.01); *A61M 5/3202* (2013.01); *A61M 5/3205* (2013.01); *B65D 75/326* (2013.01); *B65D 77/2032* (2013.01)

(58) Field of Classification Search
USPC ........................................ 206/365, 366, 364
See application file for complete search history.

(56) References Cited

U.S. PATENT DOCUMENTS

| | | | | |
|---|---|---|---|---|
| 2,023,289 | A | * 12/1935 | Pringle | ................. A61M 5/002 206/229 |
| 2,557,222 | A | * 6/1951 | Goode | ................. A61M 5/001 206/365 |
| 3,367,488 | A | 2/1968 | Hamilton | |
| 3,485,416 | A | * 12/1969 | Fohrman | ................. A47G 19/24 222/142.1 |
| 3,869,062 | A | 3/1975 | Jaeschke et al. | |

(Continued)

FOREIGN PATENT DOCUMENTS

| | | |
|---|---|---|
| EP | 2298397 A1 | 3/2011 |
| GB | 2437923 A | 11/2007 |

(Continued)

OTHER PUBLICATIONS

PCT International Search Report and Written Opinion in PCT/US2017/065691 dated Mar. 27, 2018, 14 pages.

(Continued)

*Primary Examiner* — Jacob K Ackun
(74) *Attorney, Agent, or Firm* — Servilla Whitney LLC

(57) ABSTRACT

Dual packaging for fill needles and safety needles are described herein. Such packaging can include hard packaging or blister packs. Also described herein are methods of opening the packaging and operating the needles disposed therein.

8 Claims, 9 Drawing Sheets

(56) References Cited

U.S. PATENT DOCUMENTS

| | | | | |
|---|---|---|---|---|
| 3,934,722 A | * | 1/1976 | Goldberg | A61M 5/3202 206/365 |
| 4,184,593 A | * | 1/1980 | Dorr | A61M 5/002 206/365 |
| 4,610,667 A | | 9/1986 | Pedicano et al. | |
| 4,950,242 A | * | 8/1990 | Alvarez | A61M 5/3202 604/110 |
| 5,084,027 A | * | 1/1992 | Bernard | A61M 5/3213 206/365 |
| 5,084,028 A | | 1/1992 | Kennedy et al. | |
| 5,330,899 A | | 7/1994 | DeVaughn | |
| 5,336,197 A | * | 8/1994 | Kuracina | A61M 5/3202 604/192 |
| 6,880,701 B2 | * | 4/2005 | Bergeron | A61M 5/3205 206/365 |
| 7,134,550 B2 | | 11/2006 | Groth | |
| 7,665,605 B2 | | 2/2010 | Erickson et al. | |
| 7,871,397 B2 | | 1/2011 | Schraga | |
| 8,133,200 B2 | * | 3/2012 | DiBiasi | A61M 5/3202 206/365 |
| 8,579,115 B2 | * | 11/2013 | Murphy | A61L 2/26 206/363 |
| 8,763,826 B1 | * | 7/2014 | Smith | B65D 1/0223 206/507 |
| 2002/0063074 A1 | * | 5/2002 | Simm | A61M 5/008 206/366 |
| 2003/0015444 A1 | * | 1/2003 | Molin | A61M 5/002 206/366 |
| 2003/0121815 A1 | | 7/2003 | Bergeron et al. | |
| 2004/0178098 A1 | * | 9/2004 | Swenson | A61B 17/205 206/365 |
| 2005/0067309 A1 | | 3/2005 | Choi | |
| 2005/0279664 A1 | | 12/2005 | Hommann | |
| 2006/0213793 A1 | | 9/2006 | Brand | |
| 2012/0029440 A1 | | 2/2012 | Boyd et al. | |
| 2012/0041380 A1 | * | 2/2012 | Chapin | A61M 5/002 604/192 |
| 2012/0051967 A1 | * | 3/2012 | Murphy | A61L 2/26 422/28 |
| 2014/0048433 A1 | | 2/2014 | Dasbach et al. | |
| 2014/0076758 A1 | * | 3/2014 | Dasbach | A61M 5/002 206/366 |
| 2014/0097111 A1 | * | 4/2014 | Dasbach | A61M 5/002 206/366 |
| 2015/0034516 A1 | | 2/2015 | Chapin et al. | |
| 2015/0297837 A1 | | 10/2015 | Schraga | |
| 2015/0297881 A1 | | 10/2015 | Sanders et al. | |
| 2016/0074572 A1 | | 3/2016 | Spool et al. | |
| 2016/0303331 A1 | | 10/2016 | Evans et al. | |
| 2017/0106136 A1 | | 4/2017 | Dibiasi | |
| 2017/0233168 A1 | | 8/2017 | Horvath et al. | |
| 2018/0161490 A1 | | 6/2018 | Sanders et al. | |
| 2018/0161492 A1 | | 6/2018 | Sanders et al. | |
| 2018/0161521 A1 | | 6/2018 | Sanders et al. | |

FOREIGN PATENT DOCUMENTS

| | | |
|---|---|---|
| WO | 92/06725 A1 | 4/1992 |
| WO | 02/11797 A1 | 2/2002 |
| WO | 2010/033767 A2 | 3/2010 |
| WO | 2011/107330 A1 | 9/2011 |
| WO | 2015/164416 A1 | 10/2015 |
| WO | 2016/087187 A1 | 6/2016 |

OTHER PUBLICATIONS

PCT International Search Report and Written Opinion in PCT/US2017/065692 dated Mar. 13, 2018, 14 pages.

PCT International Search Report and Written Opinion in PCT/US2017/065693 dated Mar. 7, 2018, 12 pages.

PCT International Preliminary Report on Patentability in PCT/US2017/065691 dated Jun. 27, 2019, 9 pages.

Final Office Action in U.S. Appl. No. 15/837,018 dated Jun. 18, 2019, 15 pages.

Non-Final Office Action in U.S. Appl. No. 15/837,018 dated Nov. 6, 2018, 11 pages.

Non-Final Office Action in U.S. Appl. No. 15/837,018 dated Dec. 5, 2019, 14 pages.

Non-Final Office Action in U.S. Appl. No. 15/837,020 dated Feb. 3, 2020, 11 pages.

* cited by examiner

US 10,729,843 B2

DUAL PACKAGING FOR FILL NEEDLE AND SAFETY NEEDLE

CROSS-REFERENCE TO RELATED APPLICATIONS

This application claims priority under 35 U.S.C. § 119(e) to U.S. Provisional Application No. 62/433,044, filed Dec. 12, 2016, the disclosures of which are incorporated herein by reference in their entirety.

TECHNICAL FIELD

The present disclosure generally relates to packaging for medical devices, and more particularly to dual packaging for fill needles and safety needles.

BACKGROUND

Clean or sterile articles particularly useful for medical applications are packaged to preserve their sterility. The packaging for these articles is intended to provide a barrier to prevent microorganisms from entering inside the packaging to contaminate its contents. In most instances, the packaging is opened immediately prior to using the article, such as with a blister pack housing a syringe or a needle, so as to minimize the time period in which the article is exposed to unsterile conditions.

Traditionally, practitioners that fill and inject syringes can use a one or two-needle technique. In the one-needle technique, the practitioner fills the syringe from a container (e.g. vial) having a liquid contained therein, and uses the same needle for injection. In the two-needle technique, the practitioner fills the syringe with a first needle, but replaces the needle with a new needle prior to injecting.

Both the one-needle technique and the two-needle technique offer certain advantages and disadvantages. For example, the one-needle technique is convenient because the practitioner does not have to change needles between filling and injection, but the needle can become contaminated between filling and injection. The two-needle technique allows for specialized needles that are optimized for filling and injection, but is more cumbersome for the practitioner.

Accordingly, there is a need for alternative packaging systems for providing needles.

SUMMARY

One aspect of the present disclosure pertains to a packaging system comprising a first needle, a second needle and a hard package. The first needle has a distal end and a proximal end and the second needle has a distal end and a proximal end. The hard package includes a first compartment, a second compartment, a first removable portion sealed against the first compartment, the first compartment and the first removable portion defining a first sealed region, and a second removable portion sealed against the second compartment, the second compartment and the second removable portion defining a second sealed region. The first needle can be disposed within the first sealed region such that the distance from the distal end of the first needle to the first removable portion is greater than the distance from the proximal end of the first needle to the first removable portion and the second needle can be disposed within the second sealed region such that the distance from the distal end of the second needle to the second removable portion is greater than the distance from the proximal end of the second needle to the second removable portion.

In one or more embodiments, the first needle is a blunt fill needle. In one or more embodiments, the second needle is a passive safety needle or an active safety needle.

In one or more embodiments, the distance from the distal end of the first needle to the distal end of the second needle is greater than the distance from the distal end of the first needle to the proximal end of the second needle.

In one or more embodiments, the first removable portion comprises a first pull tab. In one or more embodiments, the first removable portion is attached to the second removable portion. In one or more embodiments, the first removable portion has a perforated attachment to the second removable portion. In one or more embodiments, the second removable portion comprises a second pull tab.

Another aspect of the present disclosure pertains to a packaging system comprising a first needle, a second needle, a first hard package and a second hard package. The first needle has a distal end and a proximal end and the second needle has a distal end and a proximal end. The first hard package includes a first compartment, the second hard package includes a second compartment, and the first hard package can be attached to the second hard package. A first removable portion is sealed against the first compartment, the first compartment and the first removable portion defining a first sealed region, and a second removable portion is sealed against the second compartment, the second compartment and the second removable portion defining a second sealed region. The first needle can be disposed within the first sealed region such that the distance from the distal end of the first needle to the first removable portion is greater than the distance from the proximal end of the first needle to the first removable portion and the second needle can be disposed within the second sealed region such that the distance from the distal end of the second needle to the second removable portion is greater than the distance from the proximal end of the second needle to the second removable portion.

In one or more embodiments, the first needle is a blunt fill needle. In one or more embodiments, the second needle is a passive safety needle or an active safety needle.

In one or more embodiments, the distance from the distal end of the first needle to the distal end of the second needle is greater than the distance from the distal end of the first needle to the proximal end of the second needle.

In one or more embodiments, the first hard package is attached to the second hard package via press fitting, an adhesive bond, a solvent bond, a ring connector, a snap fit, a C-clip snap, heat staking or ultrasonic welding.

In one or more embodiments, the first hard package has a perforated attachment to the second hard package.

In one or more embodiments, the first removable portion comprises a first pull tab and the second removable portion comprises a second pull tab.

Another aspect of the present disclosure pertains to a packaging system including a first needle, a second needle and a blister package. The first needle has a distal end and a proximal end and the second needle has a distal end and a proximal end. The blister package includes a first cavity and a second cavity, the first and second cavities sealed against a backing, the first cavity and the backing defining a first sealed region, and the second cavity and the backing defining a second sealed region. The distal end of the first needle being disposed within the first sealed region and the distal end of the second needle being disposed within the second sealed region.

In one or more embodiments, the entire first needle is disposed within the first sealed region. In one or more embodiments, the entire second needle is disposed within the second sealed region.

In one or more embodiments, the first needle is a blunt fill needle. In one or more embodiments, the second needle is a passive safety needle or an active safety needle.

In one or more embodiments, the packaging system also includes a cap disposed about the proximal end of the second needle.

In one or more embodiments, the packaging system also includes a syringe. In one or more embodiments, the blister package further comprises a third cavity sealed against the backing, the third cavity and the backing defining a third sealed region, and at least a portion of the syringe is disposed within the third sealed region.

DETAILED DESCRIPTION

Figure 1:
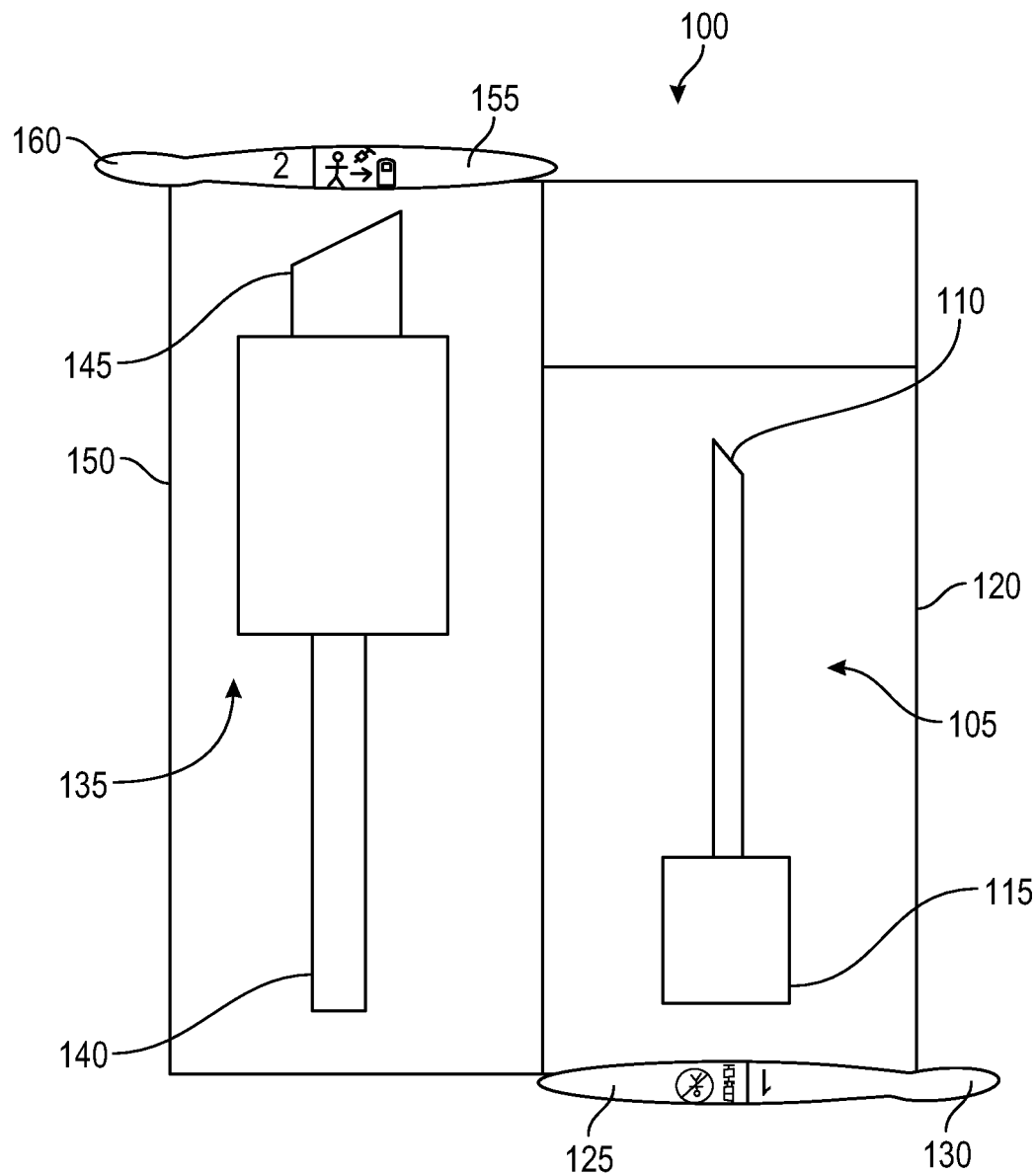
FIG. 1 illustrates a dual packaging for two needles that are oriented side-by-side in opposite directions.

Before describing several exemplary embodiments of the present disclosure, it is to be understood that the embodiments of the present disclosure are not limited to the details of construction or process steps set forth in the following description. The embodiments of the present disclosure are capable of other embodiments and of being practiced or being carried out in various ways.

With respect to terms used in this disclosure, the following definitions are provided.

As used herein, the use of "a," "an," and "the" includes the singular and plural.

Reference to "needle" includes needles that are suitable for filling and/or injecting liquids into or out of a syringe. In this disclosure, a convention is followed wherein the portion of a needle closest to the practitioner operating the needle is termed "proximal" and the portion of the needle toward the patient (for injection) or vial containing liquid (for filling) and farthest from the practitioner is termed "distal." In various embodiments, the needles described herein can be blunt fill needles, safety needles and/or conventional needles.

As used herein, a "fill needle" refers to a needle that is suitable to fill a syringe but may not be suitable for injection. For example, a fill needle may be a blunt needle that is not suitable to penetrate a patient's skin.

As used herein, a "safety needle" refers to a needle suitable for injection that includes one or more features to prevent needle stick injuries. In one or more embodiments, a safety needle includes a sheath that covers the distal end of the needle. As used herein, an "active safety needle" refers to a safety needle with a user-operated activation mechanism to cover the distal end of the needle after a patient has been injected. As used herein, a "passive safety needle" refers to a safety needle with a passive activation mechanism that automatically covers the distal end of the needle after a patient has been injected.

Reference to "syringe" includes syringes that are indicated for use with needles, nozzle, tubing, or for use in flush systems. As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel. The open end of the syringe may be fitted with a needle, nozzle, or tubing to help direct the flow of fluid into and out of the barrel. The syringe may be sterile or unsterile, depending upon the needs of the technician.

As used herein, the terms "package" or "packaging" includes any material used to wrap or protect a good or product, such as a syringe or a needle. Packaging can be rigid or flexible. Packaging includes, but is not limited to, medical packaging, pharmaceutical packaging, and child-resistant packaging. Medical and pharmaceutical packaging can include blister packs or hard packages.

As used herein, the terms "blister package" or "blister pack" includes several types of pre-formed packaging used for consumer goods, foods, pharmaceuticals, medical devices, etc. The primary component of a blister pack is a cavity or pocket made from a formable web, usually a thermoformed plastic. The formable web can be rigid or flexible. The cavity or pocket is large enough to contain the good which is housed in the blister package. Depending on the application, a blister pack may have a backing of thermoformable material and a lidding seal of aluminum foil, paper, Tyvek®, plastic, or other medical grade materials. Blister packs can also be hinged, clamshell containers, that can include a rigid backing, such as paperboard. Blister packages can provide barrier protection from microorganisms and other contaminants, and can provide a certain degree of tamper resistance. Within the many options that blister packaging provides, the blister pack must protect the product contained inside while still possessing the characteristic capable of making automated processing possible.

Blister packs are commonly used as unit-dose packaging for pharmaceutical tablets, capsules, or lozenges. The pharmaceutical product and its blister pack act together to serve as an integral unit. The blister pack protects the pharmaceutical product from outside influences that would otherwise render it useless while allowing the manufacturer of the pharmaceutical product to package it using form-fill-seal equipment. The form-fill-seal process involves creating the blister pack from rolls of flat sheet or film, filling with the pharmaceutical product, such as a drug tablet, and closing (sealing). This type of blister pack is sometimes referred to as push-through-packs because the consumer can push the good (e.g. drug tablet) through the backing. With pharmaceutical blister packs, manufacturers must be concerned with the moisture vapor transmission rate of the blister pack because many pharmaceutical products degrade and lose their efficacy through hydrolysis. Additionally, the blister pack must provide a barrier to oxygen in order to prevent degradation of the pharmaceutical product through oxidation. In one or more embodiments, the blister pack is a push-through-pack.

Blister packages that contain medical devices, such as a syringe, differ from pharmaceutical blister packs because medical blister packs are not push-through packages. Instead, the thermoformed base web is made of a thicker plastic and cannot be collapsed, thus forming a solid backing. The lidding film provides a peel-open feature that can be peeled open using two-hands, such as, e.g. the knuckle-roll-peel technique. The lidding film of a medical blister pack is generally porous to allow sterilization. Often, medical blister packs are made of Tyvek® or a similar medical grade material that is breathable and permeable to gases, but is not permeable to microorganisms. The lidding film can also be made of medical grade paper or a completely non-permeable or non-breathable film. In instances where a non-breathable film is used, sterilization is through radiation (e.g. electron beams (E-beam)). In one or more embodiments, the blister pack is a medical blister pack.

Blister packs can be created via thermoforming or cold forming. In the case of thermoforming, a plastic film or sheet is unwound from a reel and guided through a pre-heating station on the blister line. The temperature of the pre-heating plates is such that the plastic will soften and become pliable. The warm plastic then arrives in a forming station where a large pressure forms the blister cavity into a negative mold. The mold is cooled such that the plastic becomes firm again and maintains its shape when removed from the mold.

In the case of cold forming, an aluminum based-laminate film is simply pressed into a mold by means of a stamp. The aluminum elongates and maintains the formed shape. The use of aluminum offers a complete barrier for water and oxygen. However, cold form blister packs take longer to produce compared to thermoforming. Cold form blister packs are also not transparent, which can lead to consumers not complying with pharmaceutical therapies.

The thermoformable backing of the medical blister pack is generally comprised of a flexible thermoformable plastic film. The film is often multi-layered. The primary component is regularly a layer of approximately 15-30% Nylon, while the remaining layers can comprise substances including, but not limited to, polyethylene. The sealant layer can comprise, among others, ethyl vinyl acetate (EVA).

The lidding film of a medical blister pack can be made from plastic, aluminum, or medical grade papers that are permeable to gases for sterilization but are impermeable to microorganisms. Most commonly, Tyvek® is used as a lidding material for medical blister packs.

Blister packaging can also include the skin pack, where a paperboard or other backing material and product are covered with a thin sheet of transparent plastic. The backing generally has a heat-seal coating. The plastic film is softened by heat and draped over the product on the backing. Vacuum is sometimes used to assist in a snug fit. Immediately after forming the blister, the blister is transported to a vacuum sealing station where a vacuum is pulled and the blister is sealed shut, providing the snug fit. The plastic film bonds to the heat-seal coating on the paperboard or other backing. In one or more embodiments, the blister pack is a vacuum sealed thermoformed blister pack.

Blister packs can be sealed in a variety of ways including, but not limited to, heat-sealing and cold sealing. Lidding materials can have a heat-seal coating applied to them; the lidding is then sealed to the backing using heat, which activates the coating. Blister packs can also be sealed using a cold seal process, which uses a combination of a pressure sensitive fold-over blister card and a transparent blister; the blister is trapped between two pieces of board that are bonded together under pressure without using any heat. Additionally, blister packs can be sealed by orienting multiple layers of film properly in order to make a seal.

As used herein, the term "hard package" or the like includes packaging having a compartment with one or more openings that can be covered to create a seal. In one or more embodiments, the hard package includes one or more components made of a rigid material such as a rigid polymeric material. Examples of rigid polymeric materials include, but are not limited to, polyester, polycarbonate, polyethylene, polystyrene or polypropylene, or combinations or co-polymers thereof. In one or more embodiments, a hard package can be thermoformed or molded, such as by injection molding. The techniques described above for blister packs can be applied to the rigid portions of hard packages and/or to removable portions of hard packages.

As used herein, the term "microorganism" refers to a microbe or organism that is unicellular or lives in a colony of cellular organisms. Microorganisms are very diverse; they include, but are not limited to bacteria, fungi, archaea, and protozoans.

Tyvek® is a synthetic material consisting of flashspun high-density polyethylene fibers (i.e. a spunbound olefin fiber). The material is lightweight and strong, and is resistant to tearing but can be cut with scissors or a knife. Water vapor and other gases can pass through Tyvek® as the material is highly breathable, but, at the same time, the material is impermeable to liquid water and microorganisms.

As used herein, the term "sterilization" refers to a means of eliminating or killing microorganisms present on a surface, contained in a fluid or in a compound such as biological culture media in order to achieve asepsis or a sterile microbial environment. Sterilization can be achieved by applying heat, chemicals, irradiation/radiation, high pressure, filtration, or combinations thereof. Chemical sterilization includes sterilization with gases such as ethylene oxide, hydrogen peroxide gas, and ozone, liquids such as chlorine bleach, iodine, glutaraldehyde and formaldehyde, ortho-phthaladehyde (OPA), hydrogen peroxide, peracetic acid, sodium hydroxide, silver, and cobalt. Radiation sterilization involves the use of radiation such as electron beams (E-beam), x-rays, gamma rays, or subatomic particles.

As used herein, the term "knuckle-roll-peel technique" refers to the process whereby a technician, such as a doctor or nurse, opens a package to release the product contained therein. With a knuckle-roll motion, the outer packaging material is peeled apart using two hands, and the inner product is released.

Various embodiments of the present disclosure provide dual packaging systems containing two needles. In one or more embodiments, this dual packaging can help to improve work flow and efficiency for users of the two-needle technique by removing the need to remember to get two needles instead of one. In one or more embodiments, this dual packaging can also be helpful for clinicians who traditionally use a one-needle technique to fill and inject, as such practitioners may not be used to getting a separate packaged component. In one or more embodiments, this dual packaging can also help to drive compliance in clinical settings where managers want clinicians to use a two-needle technique but the clinicians would prefer to use the more convenient one-needle technique. In one or more embodiments, dual packaging can be beneficial because it helps to prevent a user from injecting a patient with a device in the fill state either accidentally or purposefully. For passive safety, injection with a device in a fill state could prevent the safety from activating. In one or more embodiments, providing two needles allows a user to perform injection with a second needle that has not been dulled, recapped, or undergone risk of touch contamination. In one or more embodiments, the two needles include a fill needle (e.g. blunt fill needle) and a needle for injection (e.g. a safety needle). In other embodiments, one or both of the needles is a conventional needle.

One or more embodiments of the present disclosure relate to a dual packaging system having a hard package. FIG. 1 illustrates an exemplary embodiment of a dual packaging system 100. A first needle 105 is disposed within a first compartment 120 and a second needle 135 is disposed within a second compartment 150. The first needle 105 has a distal end 110 and a proximal end 115 and the second needle 135 has a distal end 140 and a proximal end 145.

The first compartment 120 has an opening that is covered by a removable portion 125. The first removable portion 125 is sealed against the first compartment 120, with the first compartment 120 and the first removable portion 125 defining a first sealed region. The first removable portion 125 can include a first pull tab 130 for a user to grab in order to remove the first removable portion 125 and access the first needle 105 in the first compartment 120.

As can be seen from FIG. 1, the first needle 105 can be oriented such that the first removable portion 125 is closer to the proximal end 115 than the distal end 110. Such a configuration allows the user to grab the proximal end 115 of the first needle 105 after removing the first removable portion 125 to access the first sealed region.

The first removable portion 125 can include graphics, symbols, diagrams, words or other instructions to indicate that it is to be opened first. For example, the first removable portion 125 can include the number "1". The first removable portion may also include graphics, symbols, diagrams, words or other instructions to indicate the intended use of the first needle 105 stored in the first compartment 120. For example, if the first needle 105 is to be used for filling a syringe but not to be used to inject a patient, the first removable portion 125 can include a graphic showing a vial with a syringe and another graphic showing a human with a "Do Not" symbol around the human.

Similarly, the second compartment 150 has an opening that is covered by a second removable portion 155. The second removable portion 155 is sealed against the second compartment 150, with the second compartment 150 and the second removable portion 155 defining a second sealed region. The second removable portion 155 can include a second pull tab 160 for a user to grab in order to remove the second removable portion 155 and access the second needle 135 in the second compartment 150.

The second removable portion 155 can include graphics, symbols, diagrams, words or other instructions to indicate that it is to be opened second. For example, the second removable portion 155 can include the number "2". The second removable portion may also include graphics, symbols, diagrams, words or other instructions to indicate the intended use of the second needle 135 stored in the second compartment 150. For example, if the second needle 135 is to be used for injecting a patient, the second removable portion 155 can include a graphic showing a person with a syringe. Furthermore, if the second needle 135 is a single-use needle that locks after use, the second removable portion 155 can also include a lock symbol.

As can be seen from FIG. 1, the second needle 135 can be oriented such that the second removable portion 155 is closer to the proximal end 145 than the distal end 140. Such a configuration allows the user to grab the proximal end 145 of the second needle 135 after removing the second removable portion 155 to access the second sealed region.

Also, as can be seen from FIG. 1, the first needle 105 and the second needle 135 can be oriented side-by-side in opposite directions. That is, the distal end 110 of the first needle 105 being closer to the proximal end 145 of the second needle 135 than the distance from the distal end 110 of the first needle 105 to the distal end 140 of the second needle 135.

Figure 2:
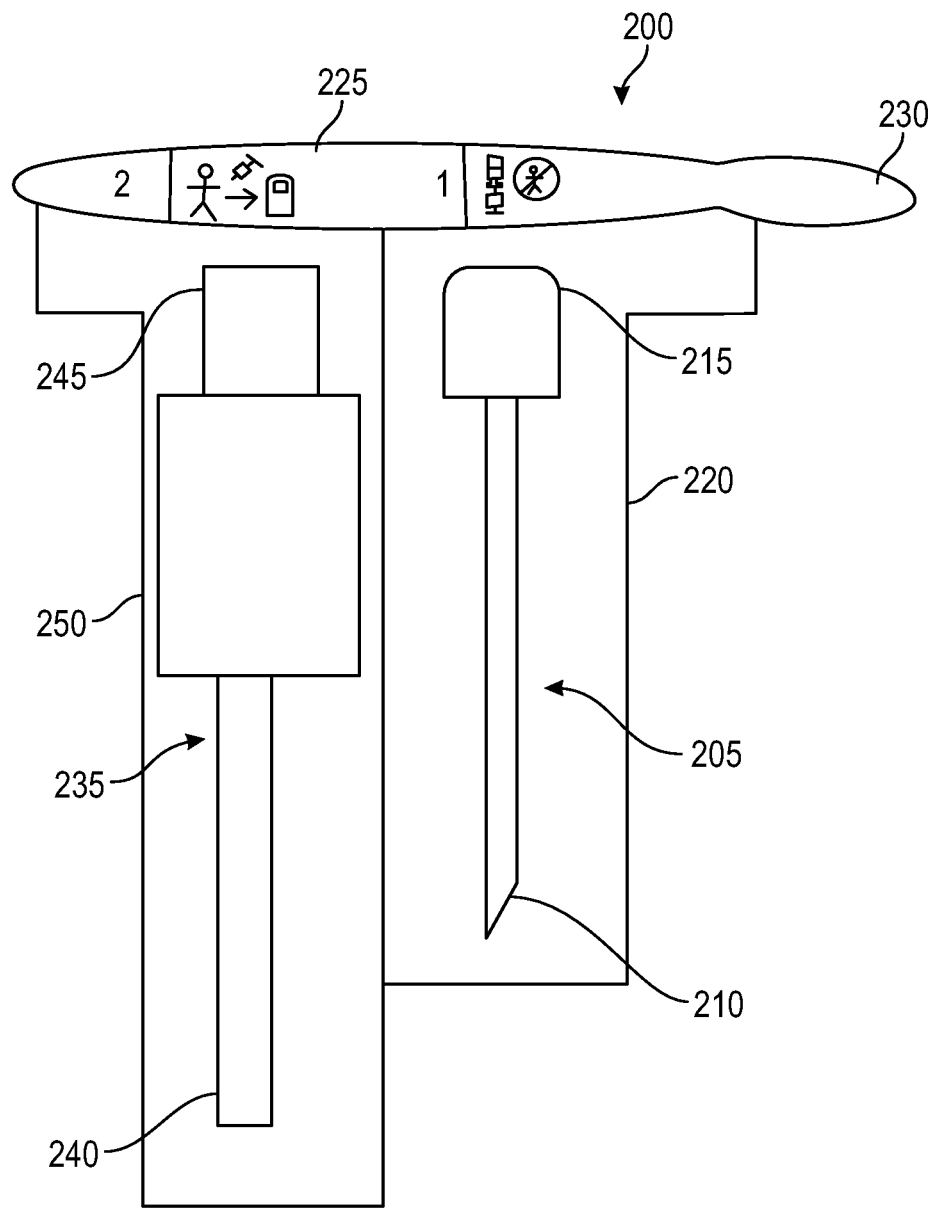
FIG. 2 illustrates a dual packaging for two needles that are oriented side-by-side in the same direction.

FIG. 2 illustrates an exemplary embodiment of a dual packaging system 200. A first needle 205 is disposed within a first compartment 220 and a second needle 235 is disposed within a second compartment 250. The first needle 205 has a distal end 210 and a proximal end 215 and the second needle 235 has a distal end 240 and a proximal end 245.

The first compartment 220 has an opening that is covered by a removable portion 225. The first removable portion 225 is sealed against the first compartment 220, with the first compartment 220 and the first removable portion 225 defining a first sealed region. The first removable portion 225 can include a first pull tab 230 for a user to grab in order to remove the first removable portion 225 and access the first needle 205 in the first compartment 220.

As can be seen from FIG. 2, the first needle 205 can be oriented such that the first removable portion 225 is closer to the proximal end 215 than the distal end 210. Such a configuration allows the user to grab the proximal end 215 of the first needle 205 after removing the first removable portion 225 to access the first sealed region.

In one or more embodiments, the second compartment 250 has an opening that is also covered by the first removable portion 225. The first removable portion 225 can be sealed against the second compartment 250, with the second compartment 250 and the first removable portion 225 defining a second sealed region. Accordingly, upon fully removing the first removable portion 225, the user may access both the first needle 205 in the first compartment 220 and the second needle 235 in the second compartment 250. Alternatively, the use may partially remove the first removable portion 225 to access the first needle 205 in the first compartment 220, and then later remove the remainder of the first removable portion 225 to access the second needle 235 in the second compartment 250.

As can be seen from FIG. 2, the second needle 235 can be oriented such that the first removable portion 225 is closer to the proximal end 245 than the distal end 240. Such a configuration allows the user to grab the proximal end 245 of the second needle 235 after removing the first removable portion 225 to access the second sealed region.

In other embodiments, the second compartment 250 has an opening that is covered by a second removable portion (not shown). The second removable portion is sealed against the second compartment 250, with the second compartment 250 and the second removable portion defining a second sealed region. The second removable portion can include a second pull tab (not shown) for a user to grab in order to remove the second removable portion and access the second needle 235 in the second compartment 250. The second needle 235 can be oriented such that the second removable portion is closer to the proximal end 245 than the distal end 240. Such a configuration allows the user to grab the proximal end 245 of the second needle 235 after removing the second removable portion to access the second sealed region.

Also, as can be seen from FIG. 2, the first needle 205 and the second needle 235 can be oriented side-by-side in the same direction. That is, the distal end 210 of the first needle 205 is closer to the distal end 240 of the second needle 235 than the distance from the distal end 210 of the first needle 205 to the proximal end 245 of the second needle 235.

The first removable portion 225 and/or second removable portion can include any of the features described above for the first removable portion 125 and second removable portion 155, such as graphics, symbols, diagrams, words or other instructions to indicate the order of opening compartments or the intended use of the needles 205 and 235 stored in the compartments.

Figure 3:
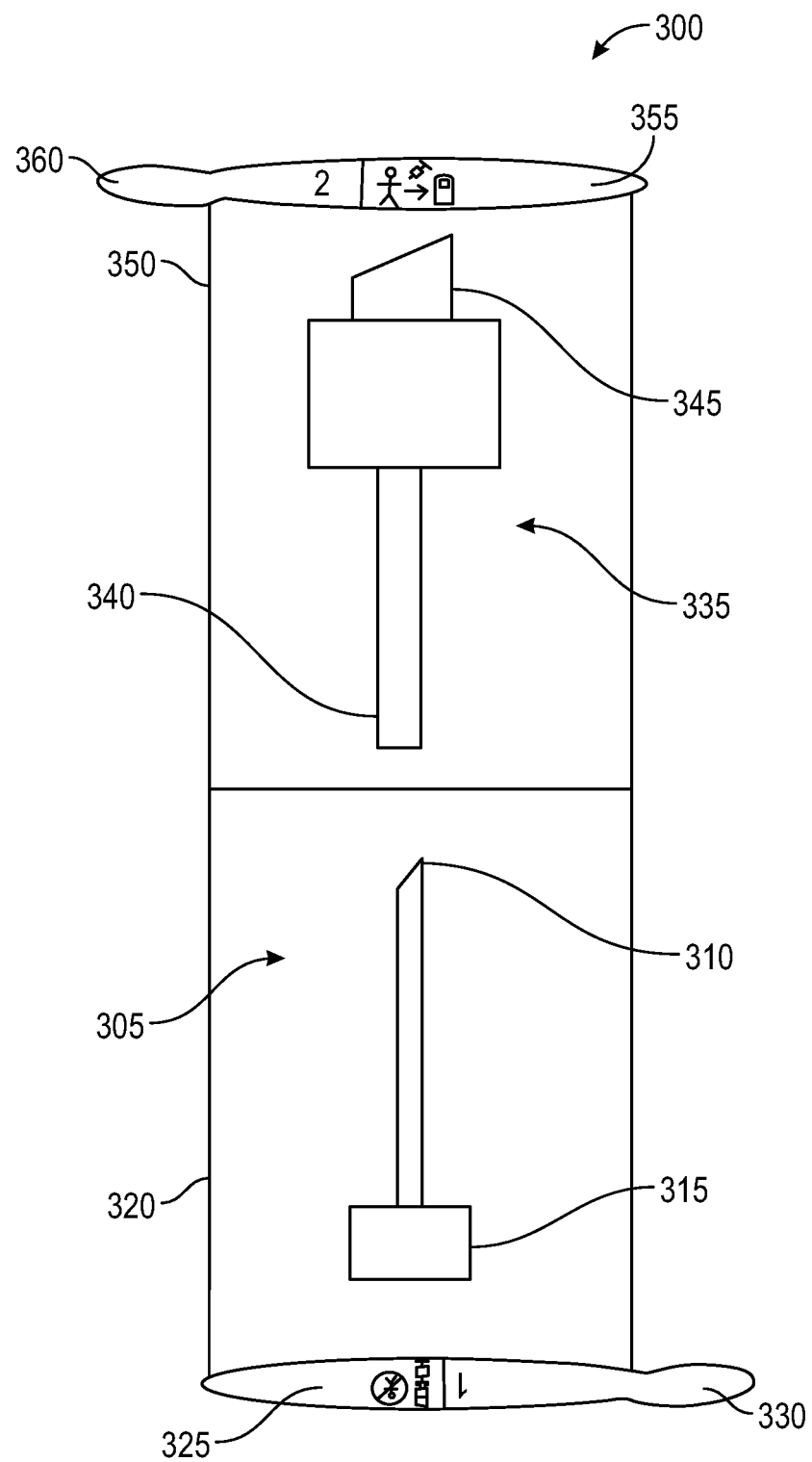
FIG. 3 illustrates a dual packaging for two needles that are oriented end-to-end.

FIG. 3 illustrates an exemplary embodiment of a dual packaging system 300. A first needle 305 is disposed within a first compartment 320 and a second needle 335 is disposed within a second compartment 350. The first needle 305 has a distal end 310 and a proximal end 315 and the second needle 335 has a distal end 340 and a proximal end 345.

The first compartment 320 has an opening that is covered by a removable portion 325. The first removable portion 325 is sealed against the first compartment 320, with the first compartment 320 and the first removable portion 325 defining a first sealed region. The first removable portion 325 can include a first pull tab 330 for a user to grab in order to remove the first removable portion 325 and access the first needle 305 in the first compartment 320.

As can be seen from FIG. 3, the first needle 305 can be oriented such that the first removable portion 325 is closer to the proximal end 315 than the distal end 310. Such a configuration allows the user to grab the proximal end 315 of the first needle 305 after removing the first removable portion 325 to access the first sealed region.

Similarly, the second compartment 350 has an opening that is covered by a second removable portion 355. The second removable portion 355 is sealed against the second compartment 350, with the second compartment 350 and the second removable portion 355 defining a second sealed region. The second removable portion 355 can include a second pull tab 360 for a user to grab in order to remove the second removable portion 355 and access the second needle 335 in the second compartment 350.

As can be seen from FIG. 3, the second needle 335 can be oriented such that the second removable portion 355 is closer to the proximal end 345 than the distal end 340. Such a configuration allows the user to grab the proximal end 345 of the second needle 335 after removing the second removable portion 355 to access the second sealed region.

Also, as can be seen from FIG. 3, the first needle 305 and the second needle 335 can be oriented end-to-end. That is, the distal end 310 of the first needle 305 can be in close proximity to the distal end 340 of the second needle 335. In one or more embodiments, a partition or barrier separates the first compartment 320 and the second compartment 350, and thus separates the first needle 305 and the second needle 335. Such a partition or barrier can be rigid, or can be soft packaging material. In other embodiments, there is no partition or barrier between the first compartment 320 and the second compartment 350.

The first removable portion 325 and second removable portion 355 can include any of the features described above for the first removable portion 125 and second removable portion 155, such as graphics, symbols, diagrams, words or other instructions to indicate the order of opening compartments or the intended use of the needles 305 and 335 stored in the compartments.

Figure 4:
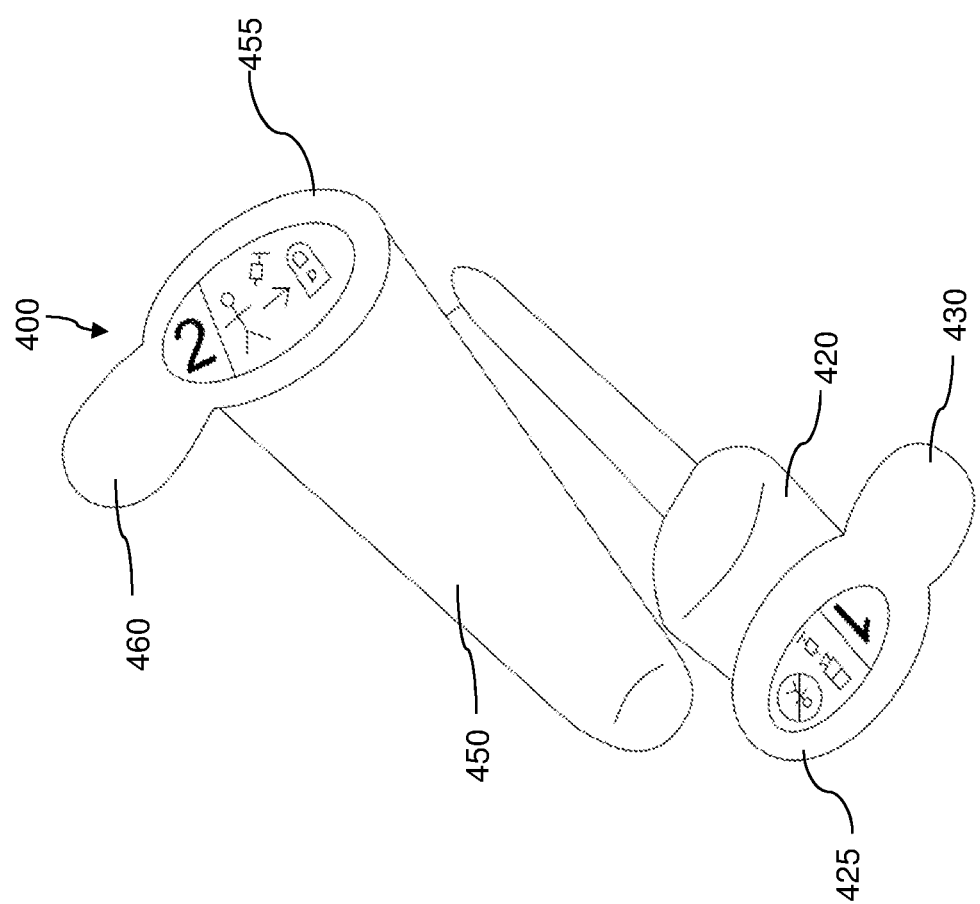
FIG. 4 illustrates a hard package having two removable portions with two pull tabs.

FIG. 4 illustrates an exemplary embodiment of a dual packaging system 400. The packing system has a first compartment 420 that can house a first needle (not shown) and a second compartment 450 that can house a second needle (not shown). As shown in in FIG. 4, the first compartment 420 and second compartment 450 can be molded in a single piece, such as by injection molding.

The first compartment 420 has an opening that is covered by a removable portion 425. The first removable portion 425 is sealed against the first compartment 420, with the first compartment 420 and the first removable portion 425 defining a first sealed region. The first removable portion 425 can include a first pull tab 430 for a user to grab in order to remove the first removable portion 425 and access the first compartment 420.

The first removable portion 425 can include graphics, symbols, diagrams, words or other instructions to indicate that it is to be opened first. For example, the first removable portion 425 can include the number "1". The first removable portion may also include graphics, symbols, diagrams, words or other instructions to indicate the intended use of the needle stored in the first compartment 420. For example, if the needle stored in the first compartment 420 is to be used for filling a syringe but not to be used to inject a patient, the first removable portion 425 can include a graphic showing a vial with a syringe and another graphic showing a human with a "Do Not" symbol around the human.

The second compartment 450 has an opening that is covered by a second removable portion 455. The second removable portion 455 is sealed against the second compartment 450, with the second compartment 450 and the second removable portion 455 defining a second sealed region. The second removable portion 455 can include a second pull tab 460 for a user to grab in order to remove the second removable portion 455 and access second compartment 450.

The second removable portion 455 can include graphics, symbols, diagrams, words or other instructions to indicate that it is to be opened second. For example, the second removable portion 455 can include the number "2". The second removable portion may also include graphics, symbols, diagrams, words or other instructions to indicate the intended use of the needle stored in the second compartment 450. For example, if the needle stored in the second compartment 450 is to be used for injecting a patient, the second removable portion 455 can include a graphic showing a person with a syringe. Furthermore, if the needle stored in the second compartment 450 is a single-use needle that locks after use, the second removable portion 455 can also include a lock symbol.

Figure 5:
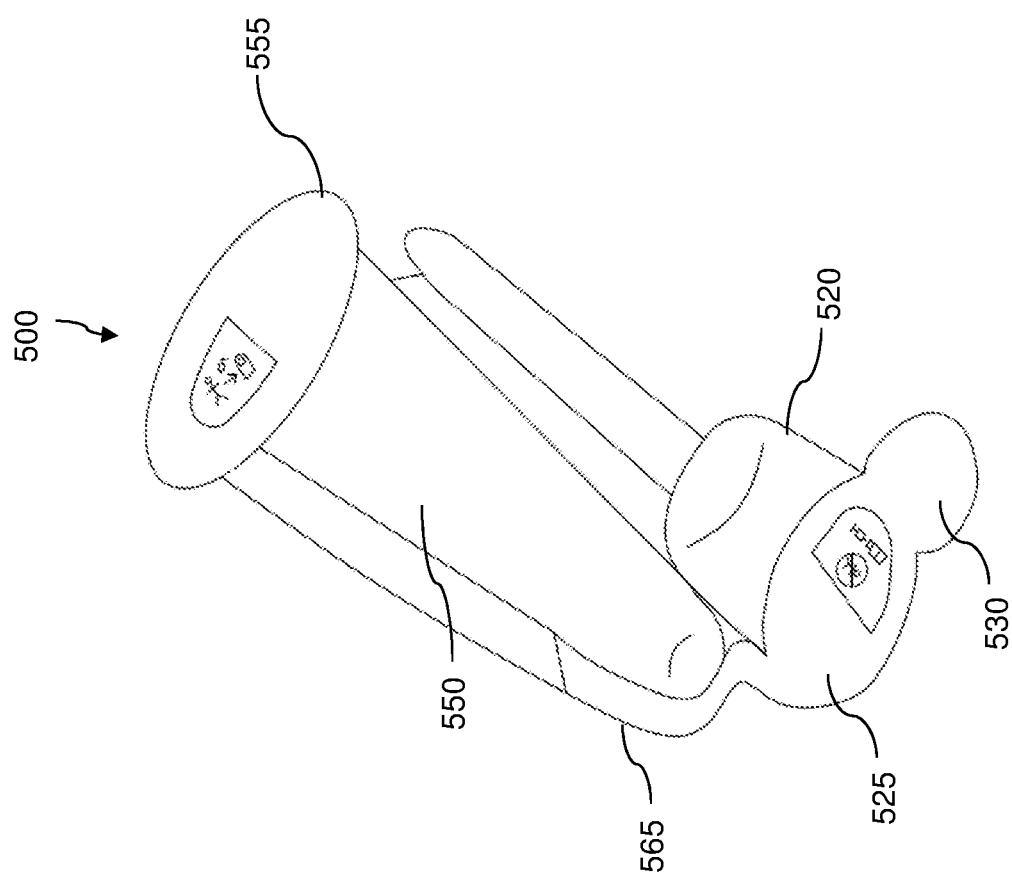
FIG. 5 illustrates a hard package having two removable portions with a single pull tab.

FIG. 5 illustrates an exemplary embodiment of a dual packaging system 500. The packing system has a first compartment 520 that can house a first needle (not shown) and a second compartment 550 that can house a second needle (not shown). As shown in in FIG. 5, the first compartment 520 and second compartment 550 can be molded in a single piece, such as by injection molding.

The first compartment 520 has an opening that is covered by a removable portion 525. The first removable portion 525 is sealed against the first compartment 520, with the first compartment 520 and the first removable portion 525 defining a first sealed region. The first removable portion 525 can include a first pull tab 530 for a user to grab in order to remove the first removable portion 525 and access the first compartment 520.

The second compartment 550 has an opening that is covered by a second removable portion 555. The second removable portion 555 is sealed against the second compartment 550, with the second compartment 550 and the second removable portion 555 defining a second sealed region. The second removable portion 555 can be attached to the first removable portion 525 via an attachment 565. After the first removable portion 525 is removed from the first compartment 520, further pulling of the removable portion 525 and/or the pull tab 530 will also remove the second removable portion 555.

The first removable portion 525 and second removable portion 555 can include any of the features described above for the first removable portion 425 and second removable portion 455, such as graphics, symbols, diagrams, words or other instructions to indicate the order of opening compartments or the intended use of the needles stored in the compartments.

Figure 6:
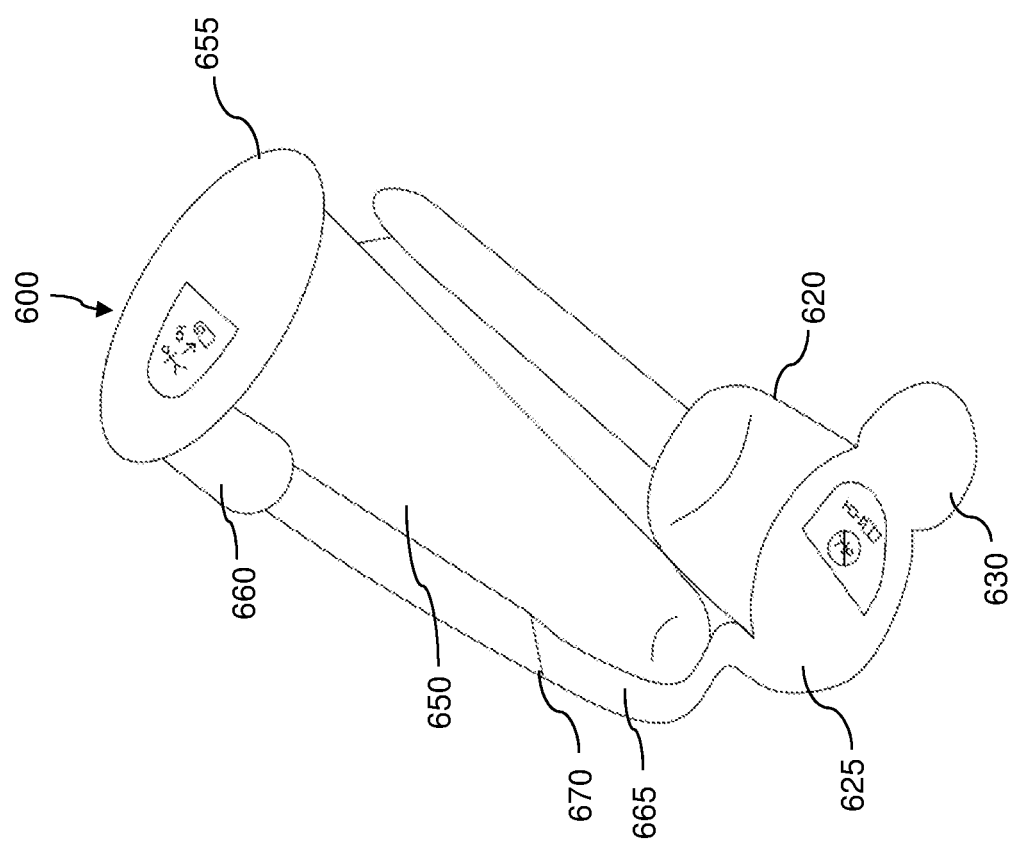
FIG. 6 illustrates a hard package having two removable portions with two pull tabs and a perforated attachment between the two removable portions.

FIG. 6 illustrates an exemplary embodiment of a dual packaging system 600. The packing system has a first compartment 620 that can house a first needle (not shown) and a second compartment 650 that can house a second needle (not shown). As shown in in FIG. 6, the first compartment 620 and second compartment 650 can be molded in a single piece, such as by injection molding.

The first compartment 620 has an opening that is covered by a removable portion 625. The first removable portion 625 is sealed against the first compartment 620, with the first compartment 620 and the first removable portion 625 defining a first sealed region. The first removable portion 625 can include a first pull tab 630 for a user to grab in order to remove the first removable portion 625 and access the first compartment 620.

The second compartment 650 has an opening that is covered by a second removable portion 655. The second removable portion 655 is sealed against the second compartment 650, with the second compartment 650 and the second removable portion 655 defining a second sealed region. The second removable portion 655 can be attached to the first removable portion 625 via an attachment 665. The attachment 665 can include a perforation 670. The perforation 670 can be located anywhere along the length of the attachment 665. After the first removable portion 625 is removed from the first compartment 620, further pulling of the removable portion 625 and/or the pull tab 630 can break the attachment 665 at the perforation 670. Further pulling of the attachment 665 can engage a pull tab 660 and remove the second removable portion 655. Alternatively, a user may pull the pull tab 660 without first pulling the pull tab 630, and the perforation 670 will allow the user to only open the second compartment 650 without also opening the first compartment 620.

The first removable portion 625 and second removable portion 655 can include any of the features described above for the first removable portion 425 and second removable portion 455, such as graphics, symbols, diagrams, words or other instructions to indicate the order of opening compartments or the intended use of the needles stored in the compartments.

Figure 7:
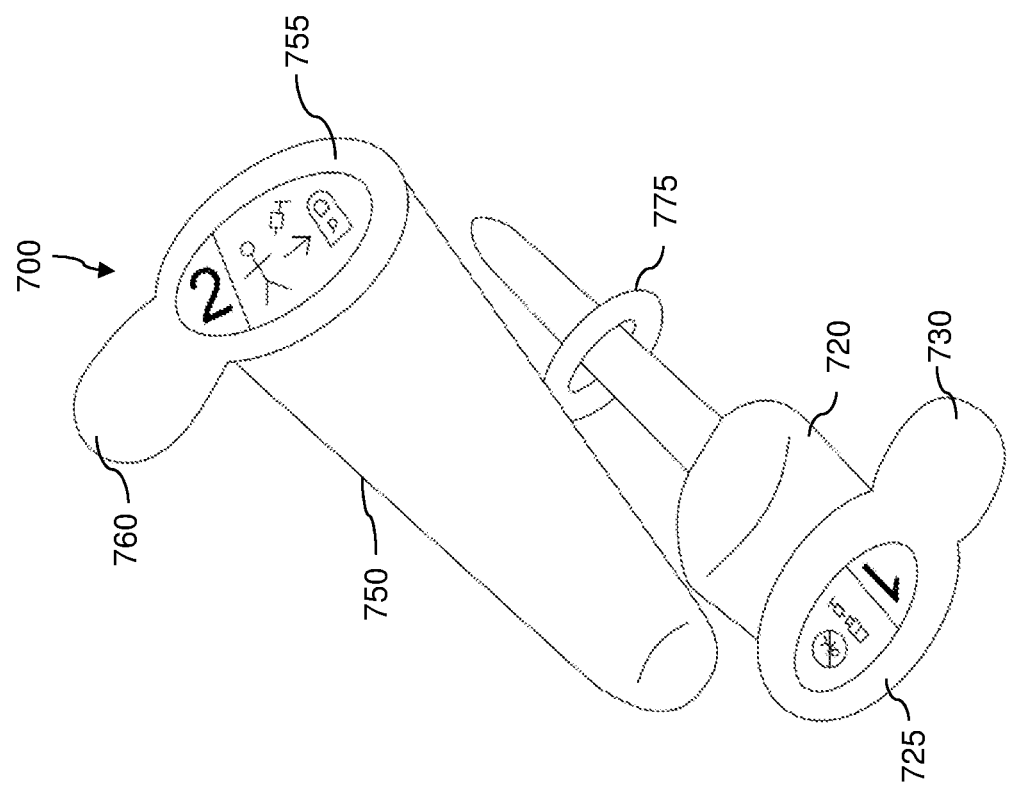
FIG. 7 illustrates two hard packages with an attachment.

FIG. 7 illustrates an exemplary embodiment of a dual packaging system 700. The packing system has a first compartment 720 that can house a first needle (not shown) and a second compartment 750 that can house a second needle (not shown). As shown in in FIG. 7, the first compartment 720 and second compartment 750 can be molded separately and joined by an attachment 775. In one or more embodiments, the first compartment 720 can be attached to the second compartment 750 via press fitting, an adhesive bond, a solvent bond, a ring connector, a snap fit, a C-clip snap, heat staking or ultrasonic welding.

In one or more embodiments, the first compartment 720 and the second compartment 750 are composed of different materials or have different colors. For example, in one or more embodiments the first compartment 720 can be colored to indicate a specific use (e.g. red to indicate a blunt fill needle) and the second compartment 750 can be clear, semi-transparent or have a different color indicating a specific use. In other embodiments, both the first compartment 720 and the second compartment 750 are clear or semi-transparent, or are the same color.

The first compartment 720 has an opening that is covered by a removable portion 725. The first removable portion 725 is sealed against the first compartment 720, with the first compartment 720 and the first removable portion 725 defining a first sealed region. The first removable portion 725 can include a first pull tab 730 for a user to grab in order to remove the first removable portion 725 and access the first compartment 720.

The second compartment 750 has an opening that is covered by a second removable portion 755. The second removable portion 755 is sealed against the second compartment 750, with the second compartment 750 and the second removable portion 755 defining a second sealed region. The second removable portion 755 can include a second pull tab 760 for a user to grab in order to remove the second removable portion 755 and access the second compartment 750.

The first removable portion 725 and second removable portion 755 can include any of the features described above for the first removable portion 425 and second removable portion 455, such as graphics, symbols, diagrams, words or other instructions to indicate the order of opening compartments or the intended use of the needles stored in the compartments.

Figure 8:
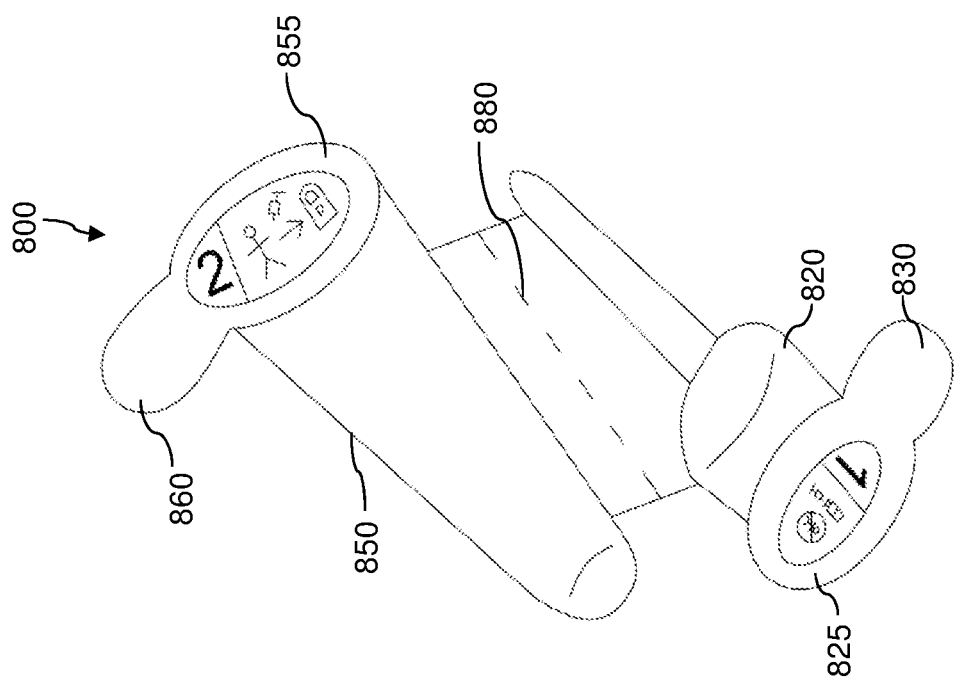
FIG. 8 illustrates two hard packages with a perforated attachment.

FIG. 8 illustrates an exemplary embodiment of a dual packaging system 800. The packing system has a first compartment 820 that can house a first needle (not shown) and a second compartment 850 that can house a second needle (not shown). As shown in in FIG. 8, the first compartment 820 and second compartment 850 can joined by a perforated or temporary attachment 880.

The first compartment 820 has an opening that is covered by a removable portion 825. The first removable portion 825 is sealed against the first compartment 820, with the first compartment 820 and the first removable portion 825 defining a first sealed region. The first removable portion 825 can include a first pull tab 830 for a user to grab in order to remove the first removable portion 825 and access the first compartment 820.

The second compartment 850 has an opening that is covered by a second removable portion 855. The second removable portion 855 is sealed against the second compartment 850, with the second compartment 850 and the second removable portion 855 defining a second sealed region. The second removable portion 855 can include a second pull tab 860 for a user to grab in order to remove the second removable portion 855 and access the second compartment 850.

The first removable portion 825 and second removable portion 855 can include any of the features described above for the first removable portion 425 and second removable portion 455, such as graphics, symbols, diagrams, words or other instructions to indicate the order of opening compartments or the intended use of the needles stored in the compartments.

Figure 9:
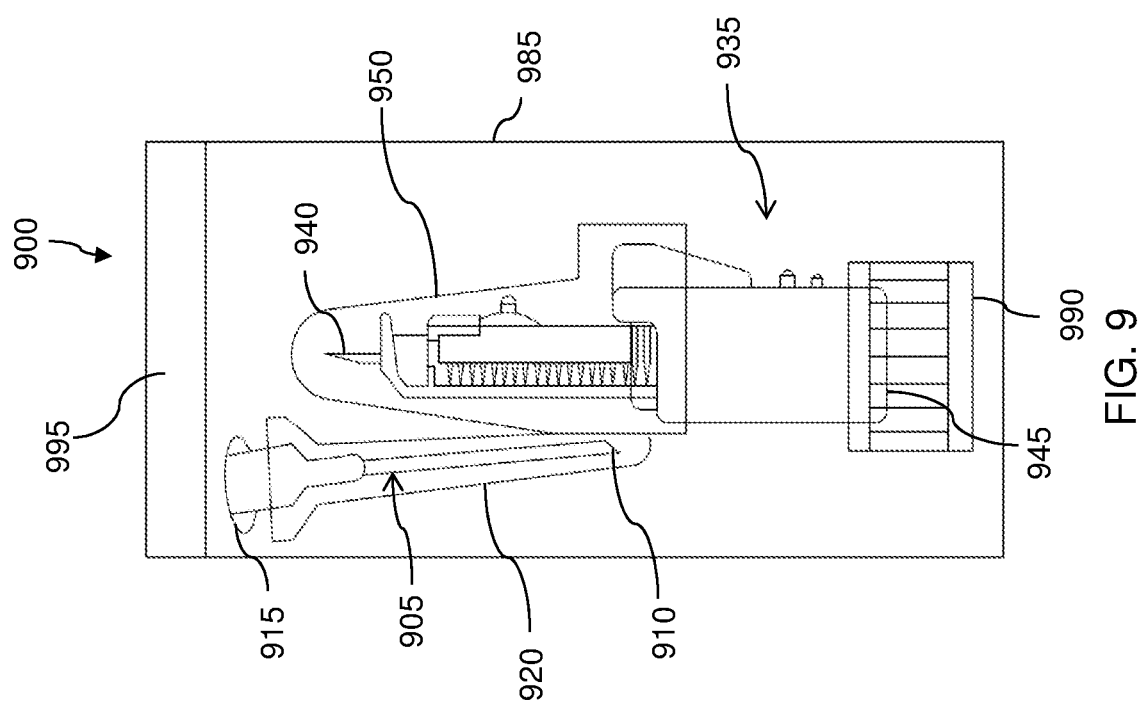
FIG. 9 illustrates a blister pack containing a blunt fill needle and a safety needle.

One or more embodiments of the present disclosure relate to a dual packaging system having a blister package. An exemplary embodiment of a dual packaging system 900 is shown in FIG. 9. A first cavity 920 houses at least a portion of a first needle 905, and a second cavity 950 houses at least a portion of a second needle 935. The distal portion 910 of the first needle 905 can be covered with a more rigid material than the proximal portion 915 of the first needle. Similarly, the distal portion 940 of the second needle 935 can be covered with a rigid material. The proximal portion 945 of the second needle 935 can be covered by a cap 990. A backing 985 can provide a seal against the first cavity 920 and the second cavity 950. The blister package can also include a peel tab 995 to open the blister package.

The blister package can also include a third cavity (not shown) housing a syringe. The third cavity can be sealed against the backing 985.

Other aspects of the present disclosure relate to methods of opening a dual packaging systems and using the needles contained therein. In one exemplary method, a practitioner opens a first compartment, removes a first needle (e.g. a blunt fill needle) and attaches the first needle to a syringe. The practitioner then fills the syringe with a liquid from a vial or other suitable container. Next, the practitioner removes the first needle from the syringe, opens the second compartment, removes a second needle (e.g. a safety needle) from the second compartment and attaches the second needle to a syringe. The practitioner then injects the patient with the liquid in the syringe. If the second needle is an active safety needle, then the practitioner may activate the mechanism to cover the distal end of the safety needle. If the second needle is a passive safety needle, then the passive activation mechanism will automatically cover the distal end of the safety needle after the patient has been injected. The practitioner may discard the used needle(s) after using each respective needle.

In another exemplary method, a practitioner opens a compartment containing two needles, removes a first needle (e.g. a blunt fill needle) and attaches the first needle to a syringe. The practitioner then fills the syringe with a liquid from a vial or other suitable container. Next, the practitioner removes the first needle from the syringe, removes the second needle (e.g. a safety needle) from compartment and attaches the second needle to a syringe. The practitioner then injects the patient with the liquid in the syringe. If the second needle is an active safety needle, then the practitioner may activate the mechanism to cover the distal end of the safety needle. If the second needle is a passive safety needle, then the passive activation mechanism will automatically cover the distal end of the safety needle after the patient has been injected. The practitioner may discard the used needle(s) after using each respective needle.

In another exemplary method, a practitioner opens a blister package containing two needles, removes a first needle (e.g. a blunt fill needle) and attaches the first needle to a syringe. The practitioner then fills the syringe with a liquid from a vial or other suitable container. Next, the practitioner removes the first needle from the syringe, removes the second needle (e.g. a safety needle) from blister package, removes a cap from the second needle, and attaches the second needle to a syringe. The practitioner then injects the patient with the liquid in the syringe. If the second needle is an active safety needle, then the practitioner may activate the mechanism to cover the distal end of the safety needle. If the second needle is a passive safety needle, then the passive activation mechanism will automatically cover the distal end of the safety needle after the patient has been injected. The practitioner may discard the used needle(s) after using each respective needle.

In another exemplary method, a practitioner opens a blister package containing two needles and a syringe, removes a first needle (e.g. a blunt fill needle) and the syringe, and attaches the first needle to a syringe. The practitioner then fills the syringe with a liquid from a vial or other suitable container. Next, the practitioner removes the first needle from the syringe, removes the second needle (e.g. a safety needle) from blister package, removes a cap from the second needle, and attaches the second needle to a syringe. The practitioner then injects the patient with the liquid in the syringe. If the second needle is an active safety needle, then the practitioner may activate the mechanism to cover the distal end of the safety needle. If the second needle is a passive safety needle, then the passive activation mechanism will automatically cover the distal end of the safety needle after the patient has been injected. The practitioner may discard the used needle(s) after using each respective needle.

In one or more embodiments of the methods described above, the user may make one or more choices throughout the method(s). For example, after opening the package, the practitioner can make one of several choices. One choice can include attaching the first needle and filling the syringe. A second choice can include removing the first needle and transporting the syringe from a first location to a second location. A third choice can include attaching the second needle and injecting the patient.

As another set of choices, the first needle can have at least two states: a fill state and a transport state. As the first choice, the practitioner can attach the first needle and choose a first state, which can be the fill state or the transport state. If the first needle is preset to the transport state to prevent needle stick injury, then the first choice can include attaching the first needle, setting the first needle to a fill state and filling the syringe. A second choice can include setting the first needle to the transport state and transporting the syringe from a first location to a second location. A third choice can include removing the first needle, attaching the second needle and injecting the patient.

As another set of choices, the second needle can have at least two states: an inject state and a transport state. As the first choice, the practitioner can attach the first needle and fill the syringe. A second choice can include removing the first needle and attaching the second needle. If the second needle is preset to the transport state to prevent needle stick injury, then the second choice can include removing the first needle, attaching the second needle and transporting the syringe from a first location to a second location. A third choice can include setting the second needle to the inject state and injecting the patient.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A packaging system comprising:
a first needle having a distal end and a proximal end;
a second needle having a distal end and a proximal end;
a hard package comprising a first compartment and a second compartment;
a first removable portion sealed against the first compartment, the first compartment and the first removable portion defining a first sealed region, the first needle being disposed within the first sealed region such that a distance from the distal end of the first needle to the first removable portion is greater than a distance from the proximal end of the first needle to the first removable portion; and
a second removable portion sealed against the second compartment, the second compartment and the second removable portion defining a second sealed region, the second needle being disposed within the second sealed region such that a distance from the distal end of the second needle to the second removable portion is greater than a distance from the proximal end of the second needle to the second removable portion;
wherein the first needle is a fill needle and the second needle is a safety needle, the fill needle being suitable to fill a syringe, the fill needle not suitable for injection, the safety needle including a needle having a distal end and an activation mechanism to cover the distal end of the needle of the safety needle;
wherein the first removable portion includes a first symbol and the second removable portion includes a second symbol, the first and second symbols indicating an order of opening compartments and intended use, the first symbol indicating that it is to be opened first and the first needle is to be used for filling a syringe but not to be used to inject a patient, the second symbol indicating the second needle is to be opened second and the second needle is to be used for injecting a patient.

2. The packaging system of claim 1, wherein the first needle is a blunt fill needle.

3. The packaging system of claim 1, wherein the second needle is a passive safety needle or an active safety needle.

4. The packaging system of claim 1, wherein the distance from the distal end of the first needle to the distal end of the second needle is greater than the distance from the distal end of the first needle to the proximal end of the second needle.

5. The packaging system of claim 1, wherein the first removable portion comprises a first pull tab.

6. The packaging system of claim 5, wherein the first removable portion is attached to the second removable portion.

7. The packaging system of claim 5, wherein the first removable portion has a perforated attachment to the second removable portion.

8. The packaging system of claim 5, wherein the second removable portion comprises a second pull tab.

* * * * *